(12) United States Patent
Savitski et al.

(10) Patent No.: US 10,224,191 B2
(45) Date of Patent: Mar. 5, 2019

(54) MS/MS DATA PROCESSING (71) Applicant: Thermo Fisher Scientific (Bremen) GmbH, Bremen (DE)

(72) Inventors: Mikhail M. Savitski, Heidelberg (DE); Roman Zubarev, Stockholm (SE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/721,469

(22) Filed: Sep. 29, 2017

(65) Prior Publication Data

US 2018/0040463 A1    Feb. 8, 2018

Related U.S. Application Data

(63) Continuation of application No. 13/846,666, filed on Mar. 18, 2013, now Pat. No. 9,786,476, which is a
(Continued)

(30) Foreign Application Priority Data

May 15, 2008 (GB) .................................. 0808876.7

(51) Int. Cl.
*H01J 49/26* (2006.01)
*H01J 49/00* (2006.01)
*G06F 19/00* (2018.01)

(52) U.S. Cl.
CPC ........ *H01J 49/0031* (2013.01); *G06F 19/703* (2013.01); *H01J 49/0045* (2013.01)

(58) Field of Classification Search
CPC .. H01J 49/0031; H01J 49/0045; G06F 19/703
(Continued)

(56) References Cited

U.S. PATENT DOCUMENTS 5,073,713 A     12/1991   Smith et al.
2005/0242279 A1  11/2005   Verentchikov
(Continued)

FOREIGN PATENT DOCUMENTS

JP   H8-124519 A      5/1996
WO   2006/103448 A2  10/2006
WO   2008/003684 A1   1/2008

OTHER PUBLICATIONS

Hengel et al., "Accidental Data Independent Collision Induced Dissociation on the LTQ-FT", Poster, Proceedings of the 54th ASMS Conference on Mass Spectrometry and Allied Topics, 2006.
(Continued)

*Primary Examiner* — Nicole Ippolito
(74) *Attorney, Agent, or Firm* — Charles B. Katz (57) ABSTRACT

A method of identifying precursor ion species from their fragments comprises obtaining mass spectra of a plurality of precursor ion species and their fragments to high mass accuracy. The fragment mass spectrum, obtained from fragmentation of multiple precursor ion species, is then scanned it identify pairs of fragments whose combined mass matches the mass of one of the precursor ion species. Once pairs of fragment ion shave been matched to precursor ions, the composite fragment ion spectrum is broken down into portions, one per fragment pair. Analysis continues until no further pairs are identified. A simplified fragment ion spectrum is then reconstructed for each precursor sample ion by stitching together the broken down sections of the composite fragment spectrum. The resultant reconstructed, simplified fragment spectra are sent to a search engine which returns a score—sorted list of likely candidates for each synthetic fragment ion spectrum.

19 Claims, 8 Drawing Sheets

Related U.S. Application Data continuation of application No. 12/992,839, filed as application No. PCT/EP2009/003175 on May 4, 2009, now Pat. No. 8,481,924.

(58) Field of Classification Search
USPC .................................. 250/281, 282, 283, 287
See application file for complete search history.

(56) References Cited

U.S. PATENT DOCUMENTS

| | | | |
|---|---|---|---|
| 2006/0243900 A1 | 11/2006 | Overney et al. | |
| 2008/0164409 A1* | 7/2008 | Schultz | G01N 27/622 250/282 |
| 2008/0173807 A1* | 7/2008 | Yoon | H01J 49/0045 250/282 |
| 2008/0272291 A1* | 11/2008 | Vestal | H01J 49/004 250/287 |
| 2009/0173877 A1 | 7/2009 | Bateman et al. | |
| 2009/0256068 A1* | 10/2009 | Petritis | C07K 1/16 250/282 |
| 2016/0005581 A1* | 1/2016 | Graichen | G01N 27/622 250/282 |

OTHER PUBLICATIONS

Masselon, et al., "Accurate mass multiplexed tandem mass spectrometry for high-throughput polypeptide identification from mixtures," Analyt. Chem., vol. 72, p. 1918-1924, (2000).

Masselon, et al., "Identification of tryptic peptides from large databases using multiplexed tandem mass spectrometry: simulations and experimental results," Proteomics, vol. 3, p. 1279-1286, (2003).

Tandem Peptide Spectrum Interpretation, http://www.weddlist.com/ms/tandem/htlm, latest update 2007.

Venable et al., "Automated approach for quantitative analysis ofcomplex peptide mixtures from tandem mass spectra", Nature Methods, 2004, vol. 1 (1), pp. 1-7.

Wilson et al., "Multiplexed MS/MS in a Quadrupole Ion Trap MassSpectrometer", Anal. Chem. 2004, 76, pp. 7346-7353.

* cited by examiner

*PRIOR ART*

MS/MS DATA PROCESSING

CROSSREFERENCE TO RELATED APPLICATIONS

The present application is a continuation under 35 U.S.C. § 120 and claims the priority benefit of co-pending U.S. patent application Ser. No. 13/846,666, filed Mar. 18, 2013, which is a continuation under 35 U.S.C. § 120 of U.S. patent application Ser. No. 12/992,839, filed Jan. 14, 2011, which is a National Stage application under 35 U.S.C. § 371 of PCT Application No. PCT/EP2009/003175, filed May 4, 2009. The disclosures of each of the foregoing applications are incorporated herein by reference.

FIELD OF THE INVENTION

This invention relates generally to the field of mass spectrometry and more specifically to a method of identifying precursor ion species from their fragments (MS/MS data processing).

BACKGROUND OF THE INVENTION

The mass spectrometric analysis of molecules is complicated by the presence of many different molecules having closely similar mass to charge ratios. Fragmentation techniques have been developed to help identify the different parent molecules by measuring the mass to charge ratios of their characteristic fragments. Ions of a molecule of interest are mass-to-charge selected by a mass selective ion optical device, along with other molecular ions of a closely similar mass-to-charge ratio. These ions are called the parent or precursor ions. These parent ions are then fragmented using one or more processes, and the fragment ions are mass analysed—providing a so-called MS/MS mass spectrum. Molecules of different structure typically fragment to form different fragment ions, and the parent molecules can be identified by studying the mass to charge ratios of those fragment ions. Where the fragment mass spectra also contain interferences, or where a higher amount of information than is present in MS/MS is required, further stages of fragmentation may be used, producing MS^n mass spectra. Libraries of protein sequences have been developed and these are searched, using algorithms developed for the purpose, to match the fragment ion spectra to likely parent molecules.

This is a powerful and widely-used method in organic mass spectrometry. However it has certain disadvantages, relating to the requirement for more than one mass selective step. This requirement increases the complexity of the instrumentation required to perform the method, and increases the time of analysis.

Besides using the technique of ion fragmentation to enable a parent molecular ion to be identified, a high mass resolution mass spectrometer may be used to distinguish between molecular ions of closely similar mass to charge ratios. However, typically such high mass resolution spectrometers are more costly and often very much slower (due to longer measurement times) than their lower resolution counterparts.

If the fragment ion mass spectra are of high resolution and high mass accuracy, the match between the fragment ions and likely parent molecules can be made with a higher degree of confidence. Consequently in order to identify large molecular ions most effectively, analysts often use a combination of high resolution mass spectrometry and fragmentation methods. However combining the two methods results in an even longer analysis time.

Methods such as those outlined above are routinely used for samples containing proteins. Typically the proteins are digested to produce peptides and these are ionised and introduced into the mass spectrometer.

The target protein or mixture (for example a cell lysate) is pre-processed. Pre-processing can include filtering or cleaning. It is then digested with a suitable cleavage reagent. The most frequently used is the enzyme trypsin, but others, like Chymotrypsin, Cyanogen bromide, iodoso benzoate are also used. After digest and possibly cleaning the mixture is fed to a mass spectrometer, usually following chromatographic separation. Chromatographic separation usually limits the time available for the tandem mass spectrometry process. Chromatography times per peak range from 30 seconds to less than 1 second with the trend being to faster times.

Initially a full mass spectrum is taken, producing a so-called precursor ion spectrum. Fragment ion spectra can be obtained for every ion species in the precursor ion spectrum (data-independent MS/MS). Alternatively, a frequently used approach is "data dependent" MS/MS. In this method, a full spectrum is acquired and afterwards the one or more most intense peaks are selected, usually automatically, and subjected to MS/MS fragmentation, one by one. The precursor and fragment spectra are stored. Various enhancements to this include: temporary blacklisting of precursors to avoid re-measurement of intense ions; permanent blacklisting of precursors to avoid collection of MS/MS data of well known peptides or solvent components; whitelisting of masses of interest to allow fragmentation even when the most intense criteria are not met. However, there are two problems with this data-dependant MS/MS approach. Firstly, different runs of the same sample may produce very different results, because, for example, even small variations in peak heights in the precursor ion spectra may result in different decisions being automatically made, leading to the selection of different precursor ion species for fragmentation. Secondly, in many cases there may not sufficient time to fragment all ions of interest within the time window available due to the preceding chromatographic process.

Figure 1:
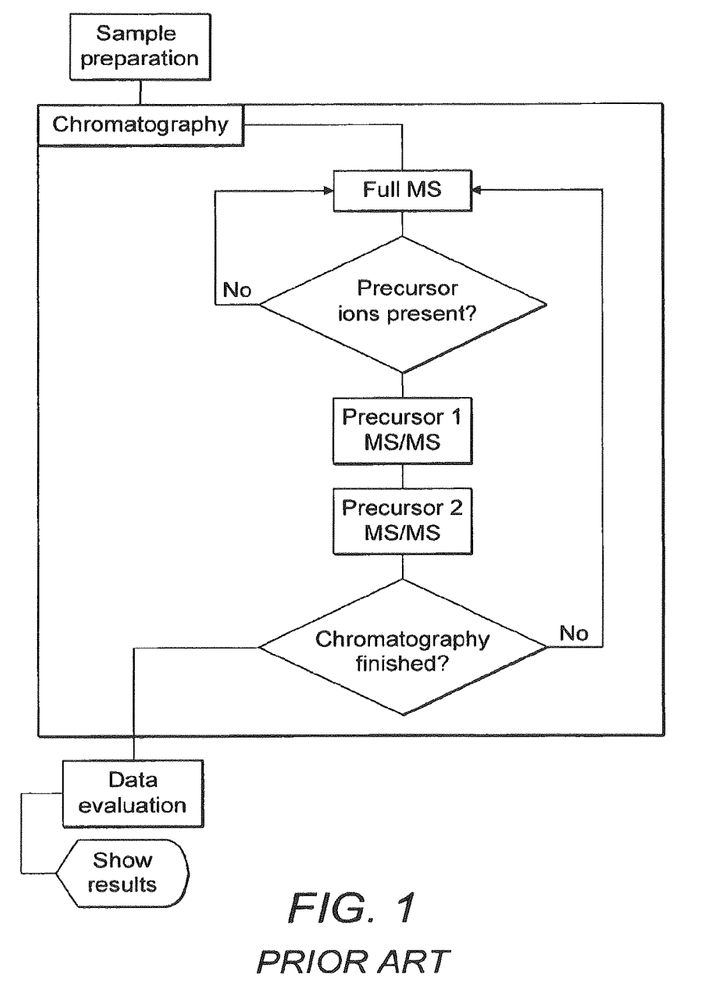
FIG. 1 shows a flow chart of a prior art data dependent process for selecting two precursor ion species for MS/MS analysis.

The prior art data-dependant process in which two precursor ions are selected for MS/MS is shown as an example in the flow chart of FIG. 1.

After, or sometimes during measurement, the acquired data are evaluated. Many methods are known for this, such as (1) "de novo sequencing" in which the amino acid sequence is inferred directly from the spectra; (2) "sequence tagging" in which only part of the amino acid sequence is directly inferred from the spectra, and these small sections ("tags") are used in a database search routine; (3) a direct database search is performed just using the fragment ion spectra.

Database searching is performed to match fragments ions to their likely peptide precursors. Automatic routines have been developed to perform the searches. The result is a list of likely precursors with a score denoting the confidence in the match. Optionally the database to be searched can be pre-selected by the user who can limit the search to peptide precursors known to be relevant, such as, for example, those for yeasts where the sample is known to have originated from a yeast. Optionally the computer search can also provide protein scores calculated from the peptide scores to give an indication of the likely proteins contained in the pre-digested sample. Typically the search algorithm returns a score-sorted list of the protein or peptide candidates along with their scores. The interpretation is then typically left to the user.

The standard approach is to submit a peak list of each of the MS/MS spectra together with the respective precursor mass (usually this is the mass that triggered the MS/MS event in the data dependent setup) to a "search engine" for comparison with a database. Normally a check for more than one precursor in the mass selection window is not done. Many databases of proteins are publicly available. Some of them directly contain proteins from previous analysis, others, such as SwissProt (http://expasy.org/sprot/), are computer translations of genomic sequences.

As the final goal of search engine use is to come up with one or more proteins determined to be in the analyte mixture, the proteins in a database are "electronically digested" to peptides with properties matching the cleavage reagent selected by the user. This "in silico digestion" can happen on the fly or as an "indexing" step before the actual search is performed. All peptides matching the precursor mass within a tolerance window defined by the user or inferred from the data are considered "candidates". Fragment ions from these candidates are then predicted. Scores are associated with these candidates based on the MS/MS data, a higher score resulting when the MS/MS fragment ion spectrum contains the predicted fragments of the predicted candidates.

Figure 2:
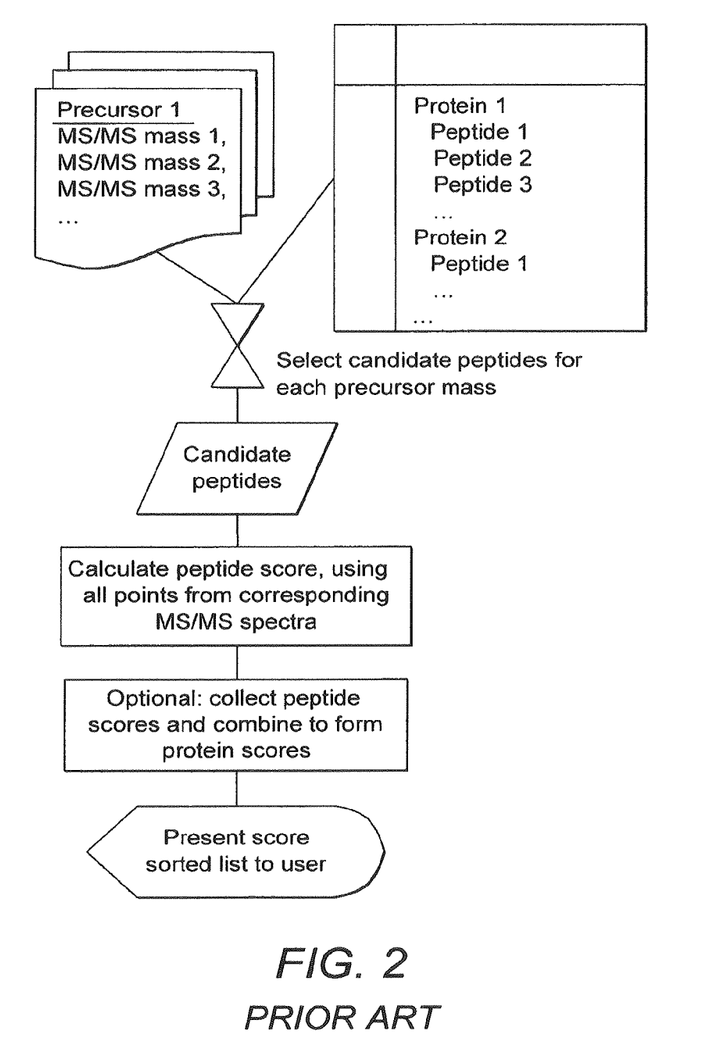
FIG. 2 shows a flow chart of a prior art database search procedure.

The prior art database search process is shown as an example in the flow chart of FIG. 2.

If deliberately or inadvertently more than one precursor ion species is selected at the same time for fragmentation, the fragment ion spectrum will be more complex and the results from the database search engine will be less accurate.

The prior art processes described in FIGS. 1 and 2 suffer from the disadvantage that the time to obtain the score-sorted list of likely peptides is slow, even where these data-dependant methods are used, because each precursor ion of interest alone must be selected and individually fragmented, and the resultant ions mass analysed sequentially, before they can be processed using standard search engine techniques. This is costly as instrument time is expensive, and it is wasteful as relatively large proportions of the sample (which may only exist in very small quantities) are consumed during the process.

One particular method of improving the throughput is described by Masselon and Smith in Analytical Chemistry, Volume 72, No. 8, pp 1918-1924, 2000. In this method a form of multiplexing is performed. Fragment ions from more than one precursor are intentionally measured in a single mass spectrum taken with very high mass accuracy. The fragment ion spectrum does then contain fragments from more than one precursor ion species. This spectrum is sent to the database search engine as normal, and the method relies on the high mass accuracy of the fragment spectrum which enables most of the fragment ions to be attributed to a specific parent polypeptide, though possibly not every fragment ion species can be assigned to a parent.

There are several disadvantages to the method of Masselon and Smith. As noted above, when fragment ion spectra from more than one precursor ion species are processed by the standard search engine methods, because the fragment ion spectra are more complex, the results from the database search engine are less accurate, even though high mass accuracy has been used. Furthermore, not only are the scores less accurate, a far greater number of false-positive identifications will result. Due to the complexity of the fragment ion spectra, the speed of the search engine is greatly reduced.

The present invention seeks to address these and other problems with prior art MS/MS data processing.

SUMMARY OF THE INVENTION

Against this background, and in accordance with a first aspect of the present invention, there is provided a method of identifying precursor ion species from their fragments comprising:

(a) determining a quantity indicative of the mass of a plurality of precursor ion species;

(b) fragmenting the ions of the plurality of precursor ion species to form a plurality of fragment ions derived from the plurality of precursor ions;

(c) mass analysing together/simultaneously, the fragment ions derived from multiple precursor ion species;

(d) assigning one or more sample sets of multiple fragment ion species to a particular one of the plurality of precursor ion species, the or each sample set including fragment ion species whose combined mass as determined in step (c)) corresponds with that of the particular one of the precursor sample ion species to which those fragment ion species are assigned;

(e) for one or more of the precursor ion species, forwarding sample data identifying (i) the mass of the particular precursor sample ion species identified in step (a), and (ii) the mass of the multiple fragment ion species in the or each assigned sample set for that particular precursor ion species, to a comparing means, for comparison of quantities indicative of the mass of the precursor and assigned fragment ion species with quantities representative of the mass of ions in one or more reference sets of reference fragment ion data and reference precursor ion data respectively; and (f) receiving, from the comparing means, information indicative of the results of the said comparison, which has sought to identify the precursor ion species to which the multiple fragment sample ion species had been assigned.

Thus, multiplexing is again used as the method of improving throughput, and fragment ion data such as a fragment mass spectrum is obtained from fragment ions derived from more than one precursor ion species. Both the fragment ion data and the precursor ion data are preferably obtained with high mass accuracy (eg <5 ppm, most preferable <2 ppm for the fragment and precursor sample ion data, with a resolving power of 100,000 at FWHM). However, instead of utilising the database search engine on this resultant fragment ion data, it is instead further processed. In this additional processing step, the fragment ion data is searched for multiple fragments whose combined mass matches that of precursor ion masses found in the precursor ion data, within certain accuracy limits. The accuracy limits may for example be determined from the mass accuracy of the fragment and parent ion data. Having matched a set or sets of multiple fragment ions to precursor ion species, the fragment ion data are broken down into portions, one portion for each precursor ion species, and containing only the set(s) of fragment ion species assigned to that particular precursor ion species. This process effectively allows the reconstruction, in preferred embodiments, of simplified fragment sample ion spectra from precursor ion species. One fragment ion spectrum may for example be produced for each precursor ion species, as though MS/MS spectra had been obtained for each precursor ion species one at a time. This process deconvolutes the multiplexing process, yet retains all the speed advantage gained by the multiplexing process. The resultant sample sets of fragment ion data (for example, deconvoluted fragment ion spectra) are then preferably sent one by one to the database search engine, which performs the standard database search on each, giving, in preferred embodiments, a score-sorted list of likely candidates for each deconvoluted fragment ion spectrum.

The method of the present invention thereby greatly improves the accuracy of the results from the database search engine. It also greatly improves the speed of search.

By the term "analysing together/simultaneously", it is meant that the method involves searching through the fragment ions from more than one precursor sample ion (whether those fragment ions are created at the same time, by simultaneous fragmentation of multiple precursors, or by accumulation together of fragments from sequential fragmentation of one or more precursors) at the same or substantially the same time. More particularly it is not intended to imply that the actual detection/identification of the fragment ions takes place as a single event. Whilst in the case of certain types of mass spectrometry such as FT-ICR or Orbitrap™ MS, the fragment ions are detected together, in others, such as TOF-MS, the ions are ejected sequentially to a detector instead. Nonetheless the analysis itself (prior to detection) is carried out on fragment ions from more than one precursor, in tandem to permit the above mentioned multiplexing.

Moreover, it will be understood that, although some preferred embodiments will determine the mass (or even the mass to charge ratio m/z) of the precursor and/or fragment ions, this is not essential to the successful operation of the invention. Many different physical parameters such as (but not limited to) time of flight, frequency, voltage, magnetic field deflection etc. might be measured (dependent for example on the chosen method of ion detection), each of which is related to or allows derivation of the ion mass or m/z. However it is not necessary that the mass itself is calculated in each case; it may be computationally more efficient not to convert measured parameters in a non-mass space into mass. Furthermore the quantity stored in the comparing database may itself not be held as a mass but instead a different quantity related to mass. Thus the term "a quantity indicative of mass" is to be interpreted broadly to encompass mass and other quantities.

Preferably, the method comprises assigning one or more pairs of fragment ions to a particular precursor ion species. This may be on the basis of a combined mass of the two fragment ion species corresponding with the mass of that assigned precursor ion species, by having a total mass that adds up to the mass of the precursor on species, or otherwise corresponds by having a predetermined offset mass from that precursor (eg as a result of neutral loss of water molecules during fragmentation). The pairs of assigned fragmentations may be so-called 'golden pairs' of ions as identified via different fragmentation techniques.

The method of the present invention also reveals ion species in the fragment sample ion data that cannot be assigned to precursor ion species in the precursor ion spectrum. These fragment ion species may or may not then be sent to the database search engine. If sent, they may be sent alone, and will not then contribute to the complexity of the other deconvoluted fragment sample ion data in the sample sets, as they would in prior art methods.

The invention may also be used to gain the speed and accuracy advantages with MS/MS/MS techniques, or MSn. Since the prior art multiplexing arrangement of Masselson and Smith in fact requires high mass accuracy for both the precursor and fragment ions, the method of embodiments of the present invention has no additional time penalty relative to that art (in terms of data collection), whilst it does in contrast provide significantly more accuracy. Of course, relative to previous methods that did not attempt to multiplex precursors, embodiments of the present invention provide for significant time savings.

Further features and advantages of the present invention will be apparent from the appended claims and the following description.

DETAILED DESCRIPTION OF A PREFERRED EMBODIMENT

Preferred embodiments of the present invention provide for a method of identifying precursor ion species from their fragments. Whilst the manner in which the fragment ions are produced is not in itself critical (and indeed, optionally, different fragmentation techniques and energies might be employed on the same precursor ions to obtain different fragment ion species), nonetheless one suitable technique for the fragmentation of precursor sample ions and the collection of mass spectrometric data from such a process will first be described so as to permit of a better understanding of the invention. It is nevertheless to be stressed that the following description of a preferred embodiment of an arrangement for fragmenting precursor ions represents merely one of many different ways of so doing, and moreover the manner in which the ions are detected is likewise capable of implementation in a variety of different ways.

Figure 3:
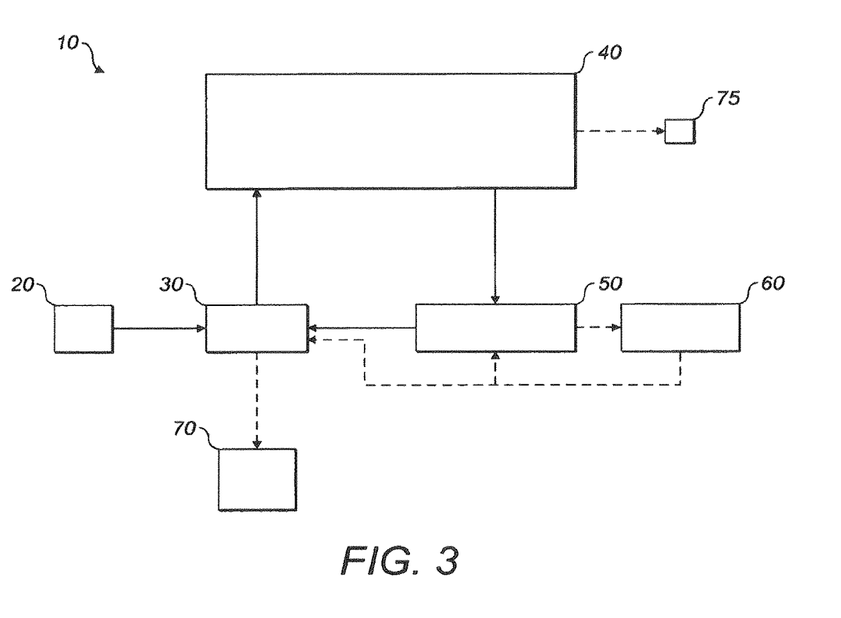
FIG. 3 shows, in block diagram form, an overview of one exemplary mass spectrometer suitable for implementing the method of embodiments of the present invention.

Referring first to FIG. 3, a mass spectrometer 10 is shown. The mass spectrometer 10 comprises an ion source 20 for generating ions to be mass analysed. The ion source 20 shown in FIG. 3 may be a pulsed laser source (preferably a matrix-assisted laser desorption ionization (MALDI) source in which ions are generated through irradiation from a pulsed laser source 22), a continuous ion source, such as an atmospheric pressure electrospray source, or otherwise.

The ions from the ion source 20 are admitted into an ion trap 30 which may, for example, be a gas-filled RF multipole or a curved quadrupole as is described, for example, in WO-A-2005/124821 and more recently in WO-A-2008/081334 whose contents are incorporated by reference.

The ions are stored in the ion trap 30, and collisional cooling of the ions may take place as is described for example in our co-pending application number WO-A-2006/103445, the contents of which are also incorporated herein by reference. Storage takes place in the ion trap 30 until the RF is switched off and a DC voltage is applied across the rods. This technique is set out in detail in our co-pending applications, published as GB-A-2,415,541 and WO-A-2005/124821, the details of which are incorporated herein in their entirety.

In a first cycle, a range of precursor ions (either contiguous across a range of m/z or a series of non-adjacent masses) is ejected from the ion trap 30 to a mass analyser 70 such as an Orbitrap, FT-ICR or other high mass accuracy analyser. This produces a high mass accuracy precursor sample ion mass spectrum for the precursor ions ejected from the ion trap 30 in the first cycle. The precursor sample ion mass spectrum serves several purposes. Firstly it may be utilized to identify a subset of precursor ions to be analysed (since not all precursor ions are likely to be of analytical interest). Secondly by obtaining the precursor spectrum at high accuracy, a measured precursor mass peak may be sent for analysis along with the fragment ion data, as explained further below.

In a second cycle, the ion trap 30 is refilled from the ion source 20. Again the ions are cooled. This time, however, rather than mass analysing all of the precursor ions together, individual precursor ions are identified for further analysis, from the previously obtained precursor sample ion mass spectrum. To isolate such identified precursor ions, the contents of the ion trap 30 are pulse-ejected towards an ion selection device which is preferably an electrostatic trap 40. Pulsed ejection produces narrow ion packets. These are captured in the electrostatic trap 40 and experience multiple reflections therein as is described in our copending application GB0725066.5 and WO-A-2007/122378.

Ejection from the ion trap 30 to the electrostatic trap 40 occurs via ion optics (not shown in FIG. 3), with optional control of the number of ions to avoid subsequent problems with space charge.

After acceleration through the ion optics the ions are focused into short packets between 10 and 100 ns long for each m/z and enter the electrostatic trap 40. On each reflection in the electrostatic trap 40, or after a certain number of reflections, unwanted ions are pulse-deflected out of the electrostatic trap 40, for example to a detector 75 or to a fragmentation cell 50. Preferably, the ion detector 75 is located close to the plane of time-of-flight focus of the ion mirrors, where the duration of the ion packets is at a minimum. Thus, only ions of analytical interest are left in the electrostatic trap 40. Further reflections will continue to increase the separation between adjacent masses, so that further narrowing of the selection window may be achieved. Ultimately, all ions having a mass-to-charge ratio adjacent to the mass-to-charge ratio m/z of interest are eliminated, leaving the single precursor sample ion species in the trap, which was identified from the precursor mass spectrum obtained in the first cycle of analysis.

That single precursor sample ion species in the electrostatic trap is then ejected to a fragmentation cell 50. Preferably, the fragmentation cell 50 is a segmented RF-only multipole with axial DC field created along its segments. The selected precursor sample ions are ejected from the electrostatic trap 40 to the fragmentation cell 50 with sufficient energy to allow them to fragment within the fragmentation cell 50.

Following fragmentation in the fragmentation cell 50, ion fragments from the first precursor ion species are transferred to an auxiliary ion storage device 60. Here they are stored whilst subsequent cycles take place, as described below.

Once the fragment ions from the first precursor sample ion species have been stored in the auxiliary ion storage device 60, the steps are repeated for a second precursor sample ion species. Specifically a second precursor sample ion species (again preferably selected based upon the precursor sample ion mass spectrum previously obtained) is isolated in the electrostatic trap 40 and then sent to the fragmentation cell 50, and fragmented, with the fragments being passed as in the previous cycle then to the auxiliary ion storage device 60 where the fragments from the second precursor sample ion being stored along with the fragments from the first precursor sample ion there.

Further cycles as above may be carried out subject to the limits of data processing (for a discussion of which, see below), subject to space charge limitations, and subject to a total ion storage time for the multiple fragment ions in the auxiliary ion storage device 60.

Once the multiple fragment ions have been accumulated in the auxiliary ion storage device 60, they are ejected back to the ion trap 30 where they enter it via a different orifice to the one from which their precursors were originally ejected as is described in detail in the aforementioned WO-A-2007/122378. From here they are ejected to the high mass accuracy mass analyser (eg Orbitrap) 70 for mass analysis. Once the mass analysis is complete, the data obtained from mass analysis of the precursor ions is processed along with the data obtained from a mass analysis of all of the fragment ions together, in a manner to be described below. The processing may take place either locally, for example in the processor of a local computer that controls or is linked to the mass spectrometer 10 (not shown), may be stored locally for subsequent analysis, and/or may be sent as one or more data files to a remote location for subsequent processing there, with the results of that processing being returned to the user of the mass spectrometer 10 subsequently.

The foregoing describes the capture of mass spectrometric data from a plurality of precursor sample ions in a first cycle, and then, by isolating each precursor ion species (identified from that precursor sample ion mass spectrum as being of interest) in successive cycles, accumulating the totality of the fragment ions from each precursor ion species by storing them together for simultaneous/parallel analysis of their fragment mass to charge ratios. However it will be understood, of course, that this is merely one way in which multiple precursor and fragment ions can be analysed at once using the techniques to be described below. For example, rather than isolating individual precursor species and then accumulating these together for fragmentation, all precursor ions may be isolated together in one step, for example using the procedure described in WO-A-2008/059246 the contents of which are incorporated by reference in their entirety.

The selection of precursors can be achieved in many different ways, which can be classified as data dependent or data independent. For example, in a data independent mode, a contiguous mass range may be selected (which may or may not include a plurality of ion species). Alternatively, a non-contiguous mass range may be selected, that is, precursors from a plurality of non-adjacent mass windows may be selected. In a data dependent mode, a predetermined number of precursor ion species may be selected (eg 4), and these may be sorted by intensity for example. "Inclusion" and "Exclusion" lists may be employed for precursor picking (which lists will be familiar to those skilled in the art), and these may optionally be dynamic lists. Other precursor identification criteria may be employed, eg Kendrick mass offset ("mass defect"), neutral loss for MS3, and so forth. Finally it may be possible to select precursors initially on the basis of certain criteria and then to carry out an additional "safety" MSn scan of the precursor ions that remain.

In terms of how the multiplexing is achieved, it will likewise be understood that the method is equally applicable both to serial analysis and fragmentation of single precursor ions (with all of the fragments being collected together in the auxiliary ion storage device 60 as described above), and to parallel analysis of multiple precursor ions (whether selected in a single cycle, or by accumulation in for example the auxiliary ion storage device 60 in multiple successive cycles), by fragmentation of the multiple precursor sample ion species together and parallel analysis of the multiple fragment sample ion species thereby produced.

Likewise, although it is desirable that the mass analysis of both precursor and fragment ions be carried out to a high mass accuracy, this can nevertheless be achieved at various locations and in various ways within the exemplary arrangement of FIG. 3. For example, precursor ions stored in the ion trap 30 may be mass-analysed in the electrostatic trap 40, by ejecting the mass from the ion trap 30 to the electrostatic trap 40, isolating the precursor ions there and ejecting them to the detector 75, rather than passing them from the ion trap 30 to the Orbitrap or other mass analyser 70. By way of example only, the detector 75 may be an electron multiplier or a microchannel/microsphere plate which has single ion sensitivity and can be used for detection of weak signals. Alternatively, the detector may be a collector and can thus measure very strong signals (potentially more than 104 ions in a peak). More than one detector could be employed, with modulators directing ion packets towards one or another according to spectral information obtained, for example, from the previous acquisition cycle. In this way, high mass accuracy data from the precursor sample ion species may be obtained via the electrostatic trap 40. Moreover, it will be understood that the manner of detection is also dependent upon the nature of the mass analysis technique being employed. For example, if time of flight mass analysis is being carried out, then ions of increasing m/z are typically detected sequentially in time via a microchannel plate for example. If on the other hand an Orbitrap or FT-MS analysis is being carried out, simultaneous detection of substantially all ions (via a time domain transient), followed by a subsequent Fourier transform into the frequency domain, may be carried out instead. From this, in turn, ion masses may be determined. It will thus be understood that mass itself need not be determined from the ion detection; time (of flight), frequency, voltage, magnetic field and other physical parameters may be the primary measured quantity and it is not necessarily essential that those primary measurement parameters are converted into ion mass. It may instead be computationally effective to bypass calculation of ion masses and do some of the subsequent analysis (to be described further below) directly in the space of the originally detected quantity. Thus, in the following, although the term "mass" (or mass to charge ratio) is employed, it is to be understood that in fact the calculations might be carried out on quantities merely related to, and not directly representative of, ion mass. Also many mass spectrometers anyway detect mass to charge ratios of ions. Various known methods exist for determination of a molecular mass from this measured m/z (see eg U.S. Pat. No. 5,072,115 and Hort et al in J Am Soc Mass Spectrometry, 2000, 11, 320-332). Most of the calculations described below are most conveniently carried out in the mass space, where possibly the charge carrying adducts are already corrected for. The necessary transformations are anyway well known in the art and/or may be readily ascertained.

Having described one exemplary way of obtaining the mass spectrometric data from a plurality of precursor sample ions and their fragments, a method embodying the present invention, which involves the processing of that data in parallel (multiplexing) so as to permit of identification of multiple precursor sample ions (or derivatives/parents thereof) substantially simultaneously, will now be described.

The composite high mass accuracy fragment sample ion mass spectrum that has been obtained, and the precursor mass spectrum, are both firstly de-charged and de-isotoped to produce simplified spectra. The fragment mass spectrum is then scanned to identify pairs of fragments whose combined mass matches the mass of a one of the precursor ion species. Complementary pairs of fragment ions have been found to possess unique specificity among all types of fragments generated through Collisionally Activated Dissociation (CAD), although other forms of fragmentation can equally be employed.

Although both the precursor and the fragment ion masses are measured to high mass accuracy, nonetheless they will still be subject to a degree of error as a consequence of the finite accuracy of the mass measurement. This measurement error may be used to inform the processing of the fragment mass information: a match may only be identified when the combined mass of the two fragment ions is the same as that of a one of the precursors to within a predetermined margin of error (or is the same as a fixed, predetermined offset from a precursor, as a result of a neutral loss of $H_2O$ etc).

Having matched pairs of fragment ions to precursor ion species, the (composite) fragment ion spectrum is broken down into portions, one portion for each fragment pair, and containing only each fragment pair. The analysis of the composite fragment mass spectrum is continued until no further pairs are identified to within the stipulated accuracy limits. Any single fragment ions left unassigned to a precursor ion species can be discarded or, included but ignored in subsequent identification analysis (described below).

Once the composite fragment spectrum analysis has been completed, one (simplified) fragment ion spectrum is reconstructed for each precursor sample ion, respectively, by stitching together or otherwise concatenating each single broken down portion of the composite fragment spectrum, for all pairs of fragment ions that have been linked to a particular precursor sample ion species. In other words, for 'n' precursor sample ions being analysed together, with a composite fragment sample ion mass spectrum obtained by fragmenting those 'n' precursor ion species (either concurrently or sequentially but with all fragments analysed together), 'n' separate simplified fragment mass spectra (containing only data from pairs of fragments having the same combined mass as a particular one of the 'n' precursors) will result from the above analysis.

The resultant deconvoluted fragment ion spectra are then sent one by one to a search engine such as Mascott™ or Sequest™ along with the measured mass to charge ratio of the associated precursor sample ion species. The search engine carries out a standard database search on each synthetic fragment spectrum, and returns a scored (and optionally score-sorted) list of likely candidates for each such deconvoluted (synthetic) fragment ion mass spectrum. Although identification of precursor ions based upon the mass of the synthetic fragment mass spectra alone is currently preferred, nonetheless the (relative) abundance of each may also be employed, optionally, to assist further with identification.

This technique deconvolutes the multiplexing process yet retains all of the speed advantage that is gained by this multiplexing process: in the prior art technique of Masselson and Smith, in fact the most accurate results are obtained when the precursor ions are accurately identified in the precursor mass spectrum and to do this it is desirable that the precursor ions are analysed at high mass resolution (and for the prior art method to work at all, it is as already discussed necessary for maximum mass accuracy of the fragment ions). In other words, embodiments of the present invention do not introduce any additional time penalty relative to the Masselson and Smith method, and provide significant time advantages over non-multiplexed MS/MS techniques. Furthermore, embodiments of the present invention do not result in a significant reduction in the accuracy of the results relative to non multiplexing techniques. In contrast to the multiplexing technique of Masselson and Smith, however, in the method now described there is no fatal drop off in the accuracy of identification of the fragment spectra as the number of multiplexed precursors increases above 2.

Figure 7:
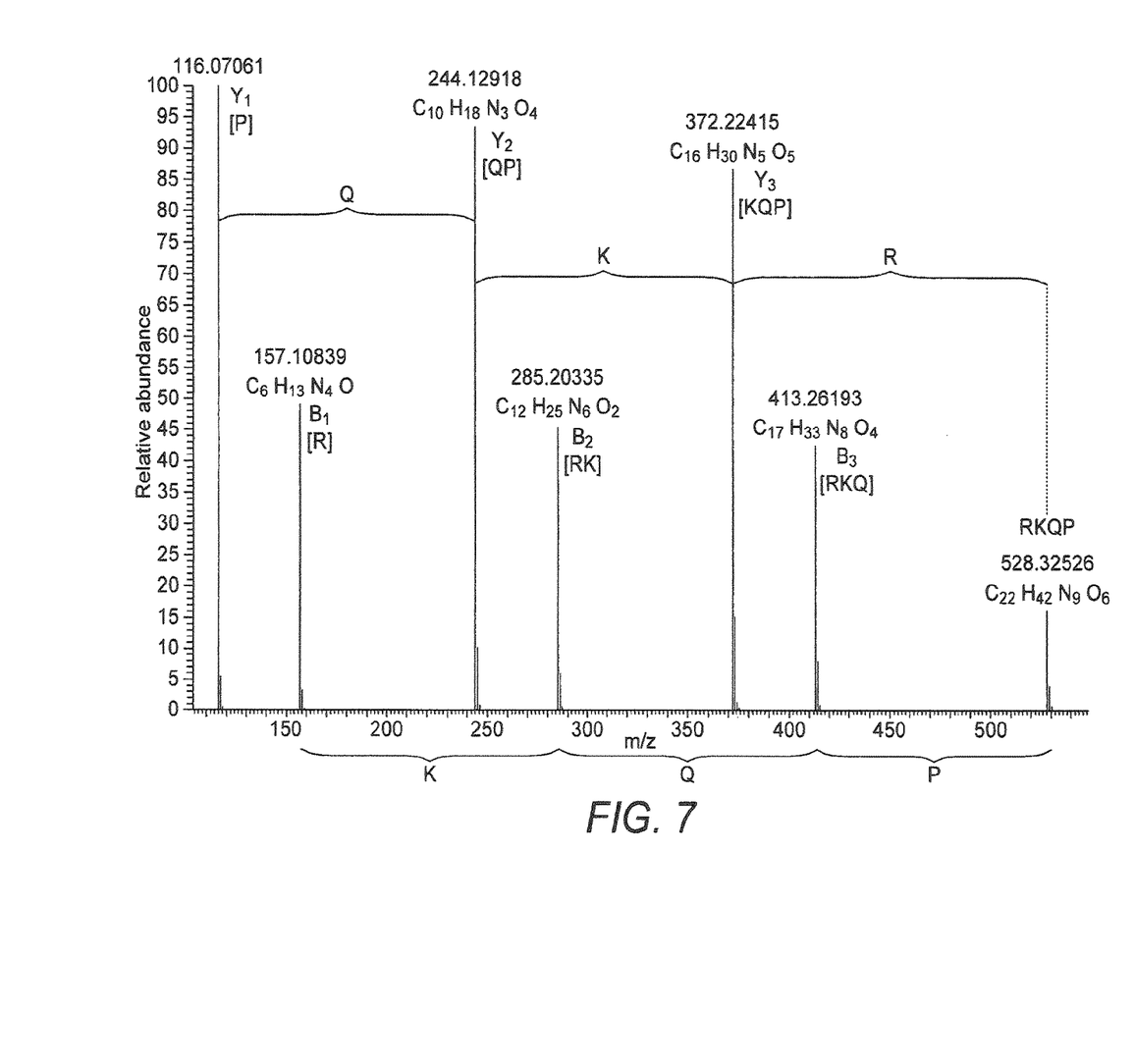
FIG. 7 shows a part of a mass spectrum for the molecule $C_{22}H_{42}N_9O_6$ and its fragments.

To illustrate further the principles described above, and in particular the method of matching fragment ion masses to a precursor ion mass, FIG. 7 shows a part of a mass spectrum for the molecule $C_{22}H_{42}N_9O_6$ and its fragments. In accordance with the techniques described above, firstly the precursor ion species ($C_{22}H_{42}N_9O_6$) is adduct corrected (the adduct is H+ with a (known) mass of 1.007825 amu). The adduct corrected mass p of the precursor is hence 528.32526−1.007825=527.317984 amu.

Next, a first fragment peak (identified in FIG. 7 as $B_1[R]$) is selected and its measured mass is again adduct corrected. The (corrected) mass $M_1$ is stored (in FIG. 7, it is noted as 157.10839−1.007825=156.101114). Next all other peaks are searched for a mass $M_2$ which, with adduct correction, has a mass M2 ($=M_2'-1.007825$) such that $M_1+M_2=p$. Once $M_2$ is identified, $M_1$ is placed in a list of verified fragment masses. The process is repeated for other fragment ions. Tables 1 and 2 show the uncorrected and adduct corrected results for the fragment ions [P] [R], [RK], [QP], [RKQ] amd [KQP] respectively (the molecular structure is shown in FIG. 7 for each fragment ion but is omitted here for brevity). It will be seen that, in each case, the pairs of adduct corrected fragment ion masses add up to the precursor ion mass when adduct corrected.

Once the list of verified fragment masses has been compiled, it may be submitted (along with details of the precursor ion mass) for further analysis, for example by a search engine as previously described.

TABLE 1

| uncorrected parent and fragment ion masses | | | | | |
|---|---|---|---|---|---|
| Fragment Name 1 | Mass of Fragment 1 | Fragment Name 2 | Mass of Fragment 2 | Parent Name | Mass of parent |
| [R] | 157.10839 | [KQP] | 372.22415 | [RKQP] | 528.32526 |
| [RK] | 285.20335 | [QP] | 244.12918 | [RKQP] | 528.32526 |
| [RKQ] | 413.26193 | [P] | 116.07061 | [RKQP] | 528.32526 |

TABLE 2

| adduct corrected parent and fragment ion masses | | | | | |
|---|---|---|---|---|---|
| Fragment Name 1 | Mass of Fragment 1 | Fragment Name 2 | Mass of Fragment 2 | Parent Name | Mass of parent |
| [R] | 156.101114 | [KQP] | 371.216874 | [RKQP] | 527.31799 |
| [RK] | 284.196074 | [QP] | 243.121904 | [RKQP] | 527.31799 |
| [RKQ] | 412.254654 | [P] | 115.063334 | [RKQP] | 527.31799 |

Figure 4:
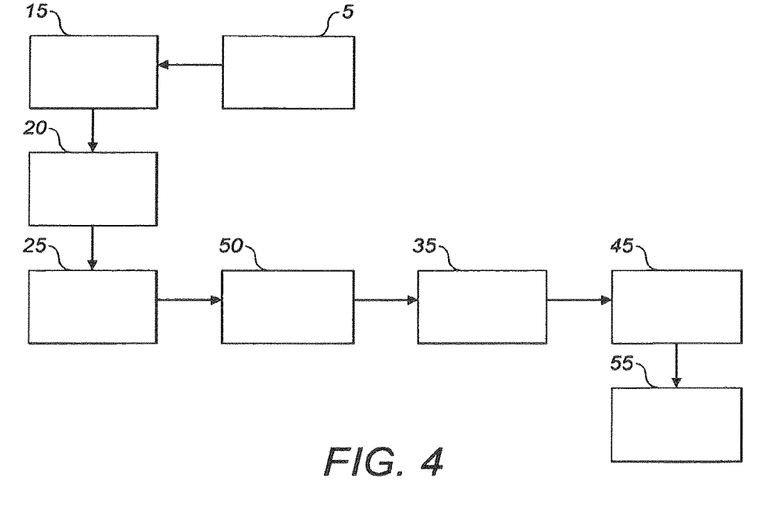
FIG. 4 shows, functionally and schematically, a second exemplary mass spectrometer suitable for implementing the methods of embodiments of the present invention.

FIG. 4 shows a functionally schematic diagram of a preferred mass spectrometer arrangement for implementation of preferred embodiments of the present invention. In FIG. 4, optional sample preparation first takes place at sample preparer 5. Chromatography (and, in particular, liquid chromatography LC) then takes place at stage 15 and the resultant molecules are ionised in an ion source 20. A first set of ions is then selected from these, in an ion selector 25. Following selection, ions are fragmented in a collision cell 50 and then collected downstream of there, in an ion collector 35.

The process of selection in the ion select 25, fragmentation in the collision cell 50, and collection in the ion collector 35 is repeated until the desired combination of ions is present in the ion collector 35. After that, ions are ejected to a mass analyser 45 (which may, for example, be an Orbitrap™ mass analyser) and the output of the mass analyser 45 is processed in a data processing system 55. The steps carried out in the data processing system 55 are as outlined above and include the steps of deconvolution of the fragment ions to separate data sets for the respective parent ions, as well as optional database search or sequencing.

Optional feedback from the data processing system 55 can be used further to control the ion selection and fragmentation processes.

It is to be understood that the arrangement of FIG. 4 is intended to be a functional representation of the preferred components of a mass spectrometer system for implementing embodiments of the present invention. Different operational stages could be executed in a single hardware element, so, for example, the steps of selection, fragmentation and collection could all be executed in a single ion trap such as the linear trap quadrupole ("LTQ") linear ion trap of an LTQ fourier transform ion cyclotron resinence (LTQ FT ICR) mass spectrometer, with only the accurate mass analysis being done in a separate mass analysing apparatus. Theoretically, even the mass analysis could be done in the same ion trap—see, for example, U.S. Pat. No. 4,755,670. Also it is to be understood that the selection of multiple ions need not be sequential. A suitable wave form, such as is described for example in U.S. Pat. No. 4,761,545, can be used to select all desired ions simultaneously in an ion trap. Similar concepts exist for mass filters.

Figure 5:
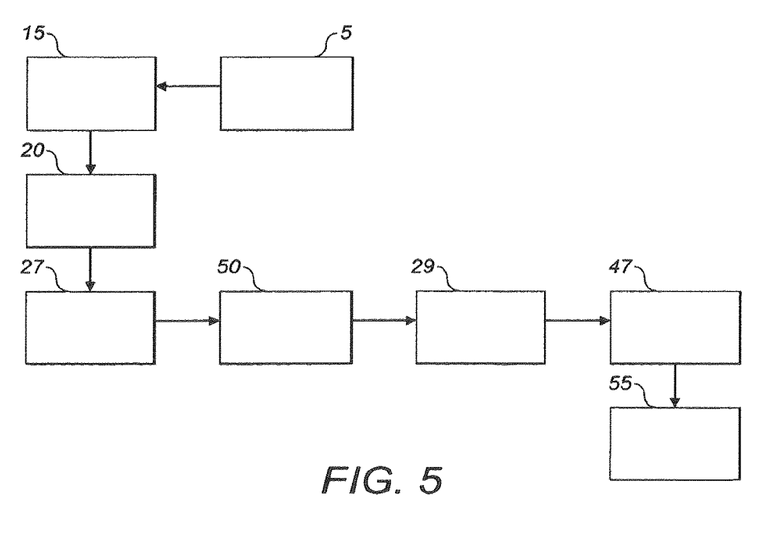
FIG. 5 shows, functionally and schematically, another exemplary mass spectrometer suitable for implementing the method of embodiments of the present invention.

Turning now to FIG. 5, a functionally schematic representation of an alternative mass spectrometer arrangement is shown, and which is suitable for implementation of preferred embodiments of the invention again. As with the arrangement of FIG. 4, sample molecules may be provided by optional sample preparation apparatus 5, coupled to a liquid chromatography arrangement 15 which supplies sample molecules to an ion source 20.

As seen in FIG. 5, the ion source 20 provides ions to a mass selection quadrupole Q 27: from there, selected ions pass to a collision cell q 50, and from there to a quadrupolar ion collector Q 29. Downstream of the quadrupolar ion collector 29 is an optional time of flight mass separator 47 connected to data processing system 55.

In typical operation of the arrangement of FIG. 5, a "normal" mass spectrum is acquired, either by scanning of the mass selection quadrupole 27, or by collection of ions in the quadrupolar ion collector 29, followed by a mass selective scan onto a detector, or by collection of ions in the quadrupolar ion collector 29 followed by mass analysis in the time of flight analyser 47.

Optionally, a decision about the following mass steps for analysis is based upon the previously acquired spectrum, although this procedure is of course not necessary when the final goal is to have all ions fragmented.

Next, the mass selection quadrupole Q 27 is operated to select the desired precursor masses or mass ranges one after another. The ions which pass through the mass selection quadrupole Q 27 are then fragmented in the collision cell q 50 and the resultant fragments are collected either directly in that collision cell q 50, thus obviating the need for the subsequent quadrupolar ion collector 29, or in that quadrupolar ion collector 29.

The resultant fragments are mass analysed in the time of flight analyser 47. Data processing, as described previously and in accordance with embodiments of the present invention, is then applied to the acquired mass information.

FIG. 6 shows, again functionally schematically, still another arrangement of a mass spectrometer suitable for implementing embodiments of the present invention. In FIG. 6, once again optional sample preparation and liquid chromatography steps may be carried out so as to provide sample molecules to an ion source 20. Ions from the ion source 20 are then directed towards a linear ion trap 26. Downstream of the linear ion trap is an ion collector 31, communicable with an ion fragmentation means 50' (which may be a collision cell) and also, separately, with an Orbitrap™ trapping mass analyser 70. The Orbitrap™ mass analyser 70 is connected to data processing system 55.

Figure 6:
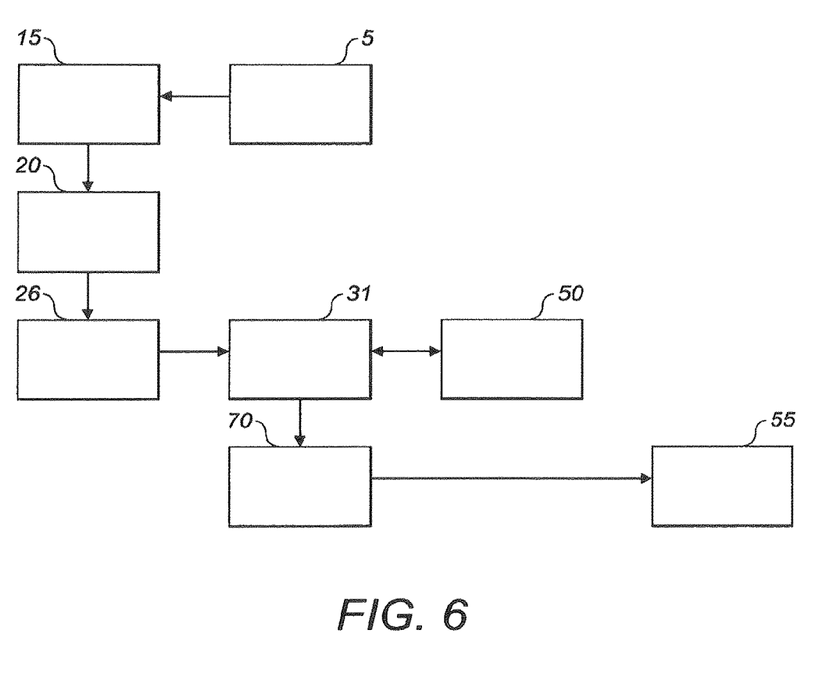
FIG. 6 shows still a further exemplary mass spectrometer, in functional and schematic form, likewise suitable for implementing the method of embodiments of the present invention

The arrangement of FIG. 6 offers multiple modes of operation. In a first mode, following a normal mass scan, a precursor ion is selected and fragmented in the linear ion trap 26. The resultant fragments are then sent to the intermediate ion store 31. The next precursor ions are treated the same way and injected into the intermediate ion store 31 to be stored alongside the previously stored fragment ions. Once all desired fragments from the different precursor ions have been collected in the intermediate ion trap 31, they are sent together to the Orbitrap™ orbital trapping mass analyser 70, for mass analysis and detection. Processing takes place at the data processing system 55 in accordance with previously described principles.

In an alternative mode of operation of the arrangement of FIG. 6, multiple precursor ions are selected at the same time, for example, with a stored waveform inverse fourier transform (SWIFT) excitation of some other form of "notched" waveform in the linear ion trap 26. The ions are then fragmented together, either in the linear ion trap 26, for example by collision induced dissociation (CID) or electron transfer dissociation (ETD), or in a separate fragmentation means 50' where high energy collision activated dissociation (HCD) may occur, the fragmentation means 50' being accessed via the intermediate ion trap 31. Fragments are then sent back out of the ion fragmentation means 50' and collected in the intermediate ion store 31. After that they may be injected into the Orbitrap™ 70 for analysis.

In still a further mode of operation of the arrangement of FIG. 6, the first and second modes described above can be combined. For example, a mass range may be isolated or different mass ranges may be isolated and added.

In yet a further mode of operation of the arrangement of FIG. 6, sequential precursor ion selection in the linear ion trap 26 may take place, with transfer to the intermediate ion store 31, followed by fragmentation of all ions together in the ion fragmentation means 50'. The resulting fragment ions are then collected in the intermediate ion store 31 again and mass analysed in the Orbitrap™ 70.

In each case, of course, once the mass data has been obtained, it can be processed using the data processing system 55 in accordance with previously described principles embodying the present invention.

Actual data from an MS/MS experiment were obtained using the method embodying the present invention. The precursor and fragment spectra were both obtained with high mass accuracy (2 ppm mass accuracy at 1 Sigma), using an FT-ICR mass analyser and with a mass resolving power of 100,000 full width at half maximum (FWHM). The database search forming the latter stages of the method was carried out with thresholds of 5 ppm (3 Sigma) and 10 ppm (6 Sigma) using the Mascot search system.

Figure 8:
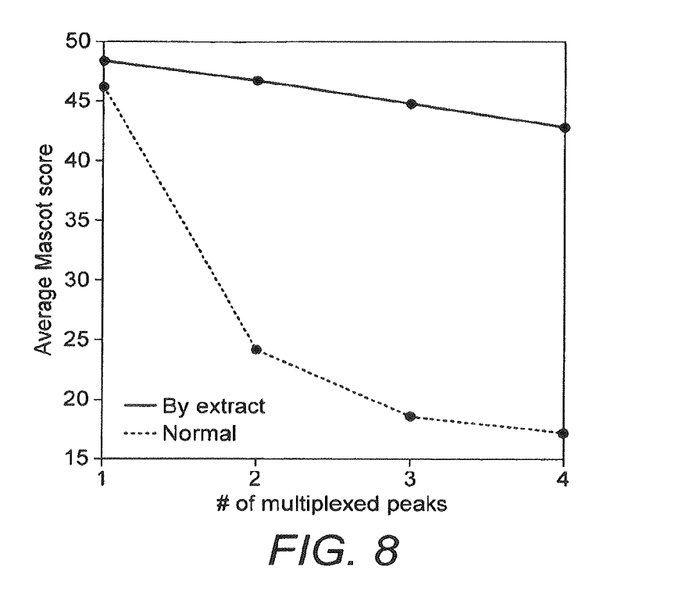
FIG. 8 shows a plot of a figure of merit for accuracy of identification of precursor ion species from experimental fragment data, as a function of the number of multiplexed sample fragment data sets, when employing a prior art method and a method in accordance with the present invention respectively.

FIG. 8 shows a plot of the average Mascot score as a function of the number of precursor ions and their fragment spectra that have been multiplexed together, using the data thus obtained and applying the methods of the present invention. For comparison, the average Mascot score obtained using the prior art Masselson and Smith technique is shown (they in fact employed the Sequest system which is similar to the Mascot system for database searching purposes).

Both methods yield reducing scores with increasing number of multiplexed peaks, but for the prior art method, the predicted score (using Mascot) falls dramatically even with only two multiplexed peaks. A score of around 30 is usually considered acceptable. It can be seen from FIG. 8 that the method of embodiments of the present invention enables many more precursor ion species to be multiplexed than the prior art methods for the same acceptable score. This results in a far greater improvement in throughput. It may also mean that far more useful information can be obtained about a sample in the time window available from the chromatographic separation which often precedes the mass spectrometry.

To obtain MS/MS data from 4 precursor ion species using a high mass accuracy spectroscopic technique, such as FT-ICR-MS or Orbitrap MS, which require ~0.5 seconds per spectral acquisition, the time taken to individually select, fragment and mass analyse is 2.5 seconds, being made up of one precursor ion spectrum and 4 fragment spectra. The time using the present invention is only one second, being made up of one precursor ion spectrum and one fragment ion spectrum. A factor 2.5 time-reduction is achieved with Mascot predicted scores staying well above the acceptable level of 30.

As noted above in relation to FIG. 8, the method of the present invention does suffer from a reducing Mascot score with increasing number of precursor ion species multiplexed, but this reduction is modest. To further illustrate this, direct comparison with non-multiplexed results has been made. One thousand mass spectra were selected from a database of CAD MS/MS spectra. Groups of four spectra were summed together to simulate the multiplexed fragment ion spectrum that would have been obtained in each case had the four precursor ion species been fragmented and the fragments combined and mass analysed together. This resulted in 250 simulated multiplexed MS/MS spectra. The processing method of the present invention was then followed, and the results compared to those obtained without multiplexing.

Following the method embodying the present invention as described above, each simulated multiplexed fragment mass spectrum was de-isotoped, de-charged, and converted to a list of neutral fragment masses. For each of the four precursor masses Mm, pairs mi and mj of fragment masses were selected, so that mi+mj=Mm within a mass uncertainty of ±15 mDa, which is related to the mass accuracy of the original spectra. Thus each simulated multiplexed mass spectrum was separated into four deconvoluted MS/MS spectra.

Figure 9:
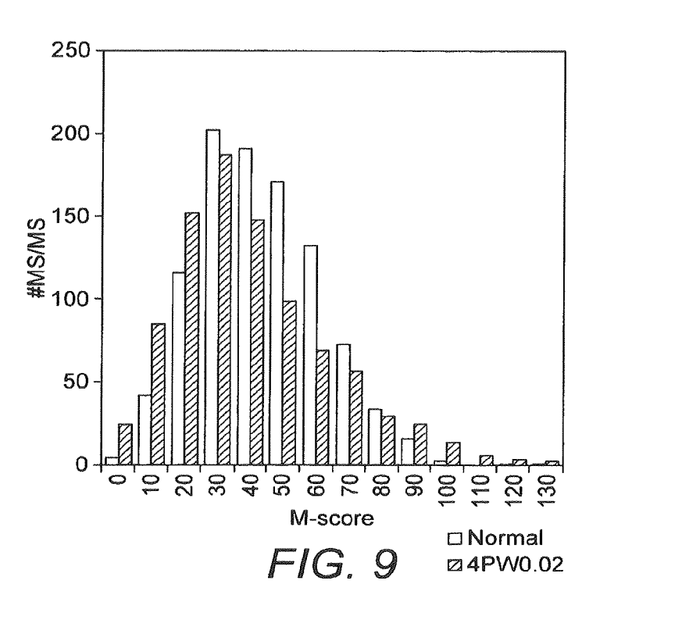
FIG. 9 shows a distribution of experimentally determined figures of merit for accuracy of identification of 1000 MS/MS spectra, when obtained individually and when obtained by multiplexing groups of 4 fragment sample ion data sets together in accordance with an embodiment of the present invention.

The original 1000 MS/MS spectra were submitted to Mascot, which resulted in 980 above-threshold peptide identifications. The remaining 20 mass spectra (0.2%) were not identified mainly because the protein database has changed after the identified spectra were put in the MS/MS database. The distribution of Mascot scores is shown in FIG. 9 by black columns. The 1000 deconvoluted mass spectra were also submitted to Mascot. In total, 899 peptides were identified (91%). The resultant distribution of Mascot scores is shown in FIG. 9 by grey columns. Sequences of only 2 deconvoluted peptides out of 899 did not coincide with the normally identified sequences, corresponding to 0.22% false positive rate.

Based upon the use of CAD to fragment the precursor ions and detection of ions in an Orbitrap mass analyser, it is possible to estimate a throughput improvement relative to a non-multiplexed MS/MS experiment. If carrying out CAD without fragment detection takes 1 time unit and Orbitrap detection takes 4 time units, then the overall time taken for a 1 in 8 cycle in "normal" (non-multiplexed) mode is 1×4 (MS) plus 8×4 (MS/MS)=36 time units. In multiplexing mode, the time taken is 1×4 (MS) plus 2×4 (MS/MS)=12 time units. Thus, there is approximately a three times throughput increase relative to a non multiplexed technique, with minimal reduction in accuracy of identification of sample ion species.

Various modifications, alternatives and additions to the techniques described above are envisaged. For example, to assist further with the process of matching pairs of fragment ion species to their precursor, the following methods may also be used.

(1) Before de-isotoping the precursor and fragment ion spectra, the fine structure of isotopic peaks may be noted, for example the presence of 13C or 32S. Such isotopes in the precursor species will also be observed in their corresponding fragments. This can be used to confirm or disprove assignments or help identify precursor-fragment relations that cannot be identified by addition of fragment pairs alone.

(2) Directly assign fragments to certain precursors when their mass fits only one of the precursors, for example when the fragment is too massive to have come from a lower mass precursor.

(3) Use accurate mass information, optionally together with information on substance class (e.g. knowledge that the sample is a peptide) to exclude/include certain fragments. Some fragments can only be from a certain precursor just by their accurate mass, the precursor accurate mass and the possible choice of neutral losses.

(4) Perform the deconvolution whilst sample analysis proceeds. Possible interferences may be identified and resolved in the next cycle of analysis of the same sample, by including the unresolved precursor ion species a second time. This subsequent cycle will produce a different multiplexed fragment spectrum as all but one precursor ion species will be different. Identification of the fragments of the previously unresolved precursor ion species can be attempted on this data set or on a combination of this and the previous set.

The foregoing describes a technique for multiplexed analysis of precursor and fragment ions in MS/MS experiments. However, it is to be understood that the invention is not limited to single stage fragmentation. In particular the methods described above are equally applicable to $MS^3$ or even $MS^n$ experiments.

Figure 10:
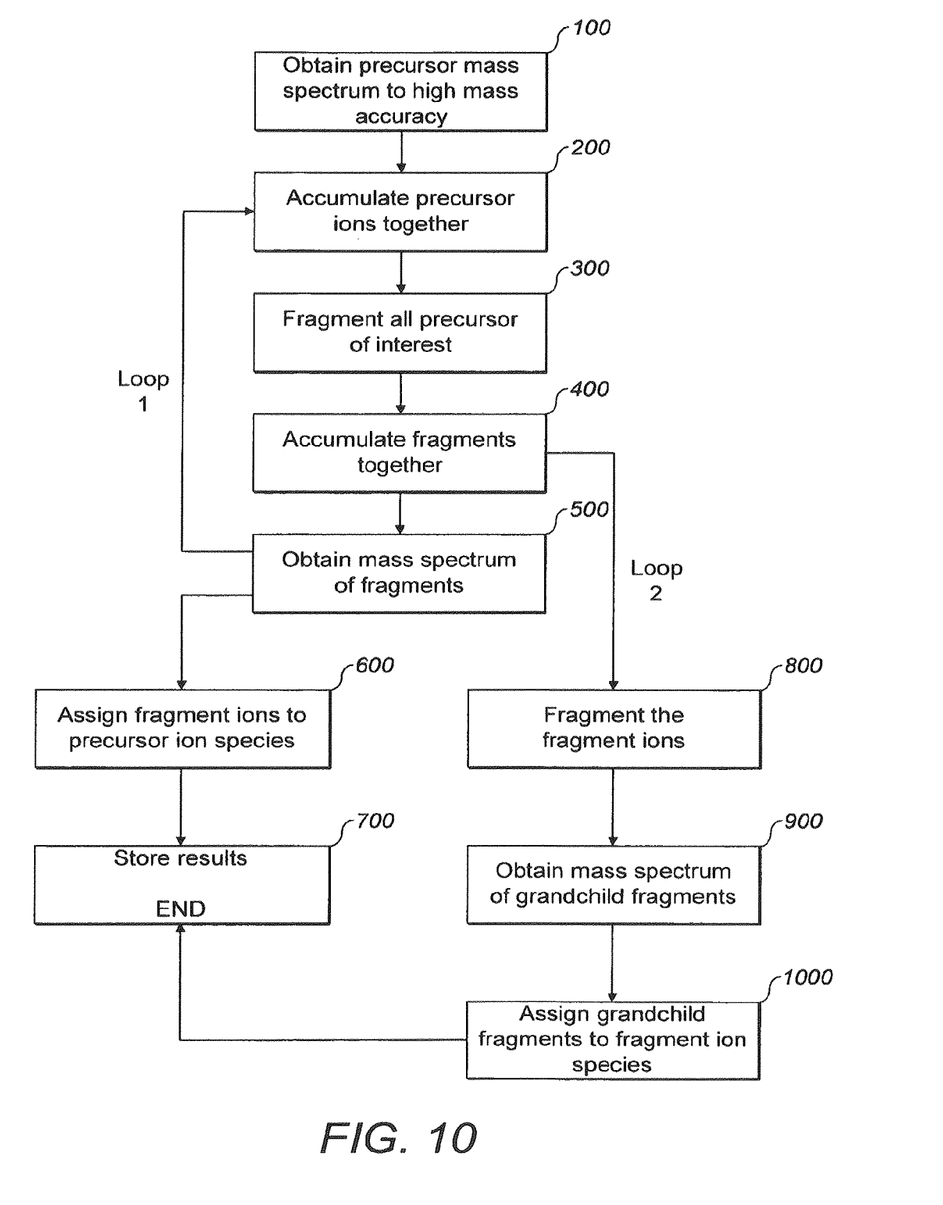
FIG. 10 shows a flow diagram of a procedure that employs the method of embodiments of the present invention, for multiple stages of fragmentation (MSn).

FIG. 10 shows a flow chart illustrating how MS3 may be carried out and, in particular, how the method of embodiments of the present invention may be applied both to first and second generation ("grandchild fragments") fragment ions. At step 100, as previously described in connection FIG. 3, a precursor mass spectrum is obtained to high accuracy, as is MS/MS. At step 200, the precursor ion species of interest are accumulated together either by multiple cycles which isolate different precursor ion species in the electrostatic trap 40, or alternatively by selecting narrower "windows" of multiple precursor ion species in the electrostatic trap 40. The accumulated precursor ion species are then fragmented together (step 300) in the fragmentation device 50 and the multiple fragment ion species from the multiple ion cursor ion species are accumulated together in the auxiliary ion storage device 60, step 400. As an alternative to the accumulation of all of the precursor ion species of interest together before fragmentation altogether, instead the precursor ion species can be isolated one at a time, fragmented individually, but still with the fragment ions from each precursor ion being accumulated together, again as previously described.

Next, at step 500, a mass spectrum of the fragments is obtained via the mass analyser 70, to high mass accuracy. The obtained mass spectrum of the fragments is sent for processing at steps 600 and 700, to be described below.

Next, in a first loop, a further set of precursor ions is accumulated (step 200 again). These are fragmented together (step 300) to form an accumulated set of first generation fragment ions which are stored in the auxiliary ion storage device 60 (step 400 again). This time, however, instead of obtaining a mass spectrum of these fragments, they are instead returned from the auxiliary ion storage device 60 back to the fragmentation device 50 where they are fragmented once more. This is shown as step 800 in FIG. 10. The resultant second generation fragment ions (grandchild fragments) are, at step 900, then mass analysed by sending them to the mass analyser 70 via the ion trap 30.

The method described above which embodies the present invention is applied to the first generation mass spectrum obtained at step 500, so as to assign fragment ions to precursor ion species (step 600). The results of that assignment are stored at step 700. Likewise, the mass spectrum of the second generation (grandchild) fragment ions is analysed using the technique of embodiments of the present invention so as to assign second generation fragment ions to first generation fragment ion species. This is shown at step 1000. Again the results of that analysis are stored at step 700.

Applying techniques of the present invention to multiple stages of mass spectrometry (MSn) provides for a potentially very significant time saving relative to the prior art. The step 100 of obtaining a spectrum of the precursor ions takes approximately 0.5 seconds. Obtaining the mass spectrum of the first generation fragment ions (step 500) likewise takes 0.5 seconds, and it may even be possible to dispense with this step entirely when MS3 is being employed. Finally, the mass spectrum of second generation fragment ions at step 900 takes about 0.5 seconds.

Thus, at worst, the total data collection time is 1.5 seconds. The prior art techniques take at least 10.5 seconds because the four separate fragment ion spectra take approximately 2 seconds to obtain and the sixteen consequential second generation fragment spectra take 8 seconds in total.

Clearly, the technique becomes more complicated as further generations of fragments might be obtained but, equally, the time saving becomes higher. One of the purposes of MS3 experiments is to disambiguate neutral fragments such as water, ammonia, phosphorylation or other side chain losses, and loss of sugars from glycopeptides.

Furthermore, although the foregoing describes the analysis of fragment ions generated through CAD, it is to be understood that the techniques are equally applicable to many other forms of ion fragmentation such as (but not limited to) ECD, ETD, metastable ion bombardment, CID (both trap CID and HCD), and IRMPD, for example. Indeed, as yet another variation to the methods described above, and in order to yield further information, the isolation of precursor ion species and the subsequent fragmentation may be repeated but with the fragmentation methods and/or the fragmentation energies varied for the same precursor ion species. This technique allows potential identification of so-called "golden pairs" of fragments where the different fragmentation techniques produce different cleavage mechanisms which are more or less understood. For example, a B2 fragment produced by collisionally inducted dissociation (CID) may match a corresponding C2 fragment in ETD, with a fixed mass difference of 17.0265 being the mass of ammonia (NH3).

The method of the present invention can be applied to the analysis of polymers and biopolymers such as proteins, peptides, DNA/RNA, lipids and modifications of these.

The invention claimed is:

1. A method of analyzing a sample by mass spectrometry, comprising:
acquiring a precursor mass spectrum of precursor ions derived from the sample;
selecting a plurality of precursor ion species in a mass range;
fragmenting the plurality of precursor ion species to produce fragment ions;
analyzing together/simultaneously the fragment ions to generate a fragment ion mass spectrum; and
deconvoluting the fragment ion mass spectrum to obtain one or more deconvoluted sample sets of fragment ion data each representing a different one of the precursor ion species, by assigning a set of fragment ion species present in the fragment ion mass spectrum to the corresponding precursor ion species of the one or more sample sets.

2. The method of claim 1, wherein the step of selecting the plurality of precursor ion species comprises selecting a contiguous mass range.

3. The method of claim 1, further comprising a step of performing a database search of the one or more deconvoluted sample sets of fragment ion data to generate a score-sorted list of likely identifications for each deconvoluted sample set.

4. The method of claim 1, wherein the sample contains proteins.

5. The method of claim 1, wherein the step of acquiring the precursor mass spectrum is performed in a high mass accuracy analyzer.

6. The method of claim 5, wherein the high mass accuracy analyzer is an electrostatic trap analyzer.

7. The method of claim 1, wherein the step of deconvoluting the fragment ion mass spectrum comprises identifying a set of fragment ion species having aggregate masses that approximate the corresponding precursor ion species.

8. The method of claim 1, wherein the set of fragment ion species includes at least two fragment ion species.

9. The method of claim 1, wherein the precursor ion spectrum is acquired at a mass accuracy of less than 5 parts per million (ppm).

10. The method of claim 1, wherein the step of fragmenting the plurality of precursor ion species is performed by collisionally activated dissociation (CAD).

11. The method of claim 1, further comprising constructing a simplified fragment ion spectrum for each one of the plurality of precursor ion species.

12. The method of claim 2, wherein the step of selecting the plurality of precursor ion species comprises operating a mass selection quadrupole to selectively transmit ions in the contiguous mass range.

13. The method of claim 1, wherein the step of acquiring the precursor mass spectrum is performed in a time-of-flight analyzer.

14. The method of claim 1, wherein the steps of selecting, fragmenting and analyzing are repeated in cycles, the mass range of precursor ions selected in each cycle being different.

15. A mass spectrometer, comprising:
an ion source for generating precursor ions from a sample to be analyzed;
a mass selector for selecting a mass range of ions;
a collision cell positioned to receive the selected precursor ions from the mass selector and to cause the selected precursor ions to fragment into fragment ions;
a mass analyzer for mass analyzing ions and generating a spectrum therefrom; and
a controller programmed with instructions for:
causing the mass analyzer to acquire a precursor mass spectrum;
causing the mass selector to select a plurality of precursor ion species and pass the selected precursor ion species to the collision cell to form fragment ions;
causing the mass analyzer to mass analyze together the fragment ions formed from the plurality of precursor ion species to generate a fragment ion mass spectrum; and
deconvoluting the fragment ion mass spectrum to obtain one or more deconvoluted sample sets of fragment ion data each representing a different one of the precursor ion species, by assigning a set of fragment ion species present in the fragment ion spectrum to the corresponding precursor ion species of the one or more sample sets.

16. The mass spectrometer of claim 15, wherein the mass selector is a quadrupole mass selector configured to selectively transmit ions within a contiguous mass range.

17. The mass spectrometer of claim 15, wherein the mass analyzer is a high mass accuracy mass analyzer.

18. The mass spectrometer of claim 17, wherein the mass analyzer is an electrostatic trap mass analyzer.

19. The mass spectrometer of claim 15, wherein the mass analyzer is a time-of-flight mass analyzer.

* * * * *